United States Patent
Pavliv et al.

(10) Patent No.: US 12,161,632 B2
(45) Date of Patent: *Dec. 10, 2024

(54) COMPOSITIONS AND METHODS OF TREATING CARDIAC FIBROSIS WITH IFETROBAN

(71) Applicants: Cumberland Pharmaceuticals Inc., Nashville, TN (US); Vanderbilt University, Nashville, TN (US)

(72) Inventors: Leo Pavliv, Cary, NC (US); Bryan Voss, Nashville, TN (US); James West, Nashville, TN (US); Erica Carrier, Nashville, TN (US)

(73) Assignees: Cumberland Pharmaceuticals Inc., Nashville, TN (US); Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/132,480

(22) Filed: Apr. 10, 2023

(65) Prior Publication Data

US 2023/0270726 A1    Aug. 31, 2023

Related U.S. Application Data

(63) Continuation of application No. 17/151,181, filed on Jan. 17, 2021, now abandoned, which is a continuation of application No. 16/752,933, filed on Jan. 27, 2020, now Pat. No. 10,925,860, which is a continuation of application No. 16/391,444, filed on Apr. 23, 2019, now Pat. No. 10,583,126, which is a continuation of application No. 16/004,666, filed on Jun. 11, 2018, now Pat. No. 10,314,824, which is a continuation of application No. 15/608,507, filed on May 30, 2017, now Pat. No. 10,016,399, which is a continuation of application No. 14/715,143, filed on May 18, 2015, now Pat. No. 9,693,998.

(60) Provisional application No. 62/118,896, filed on Feb. 20, 2015, provisional application No. 62/078,649, filed on Nov. 12, 2014, provisional application No. 61/994,436, filed on May 16, 2014.

(51) Int. Cl.

| | |
|---|---|
| A61K 9/00 | (2006.01) |
| A61K 9/20 | (2006.01) |
| A61K 9/48 | (2006.01) |
| A61K 31/421 | (2006.01) |
| A61K 31/422 | (2006.01) |
| C07D 263/30 | (2006.01) |
| C07D 407/04 | (2006.01) |
| C07D 413/04 | (2006.01) |
| C07D 493/08 | (2006.01) |

(52) U.S. Cl.
CPC ............ *A61K 31/421* (2013.01); *A61K 9/00* (2013.01); *A61K 9/0019* (2013.01); *A61K 9/2059* (2013.01); *A61K 9/4858* (2013.01); *A61K 31/422* (2013.01); *C07D 263/30* (2013.01); *C07D 407/04* (2013.01); *C07D 413/04* (2013.01); *C07D 493/08* (2013.01)

(58) Field of Classification Search
CPC .. A61K 31/421; A61K 31/422; A61K 9/0019; A61K 9/2059; A61K 9/4858; A61K 9/00; C07D 263/30; C07D 407/04; C07D 413/04; C07D 493/08
See application file for complete search history.

(56) References Cited

U.S. PATENT DOCUMENTS

| | | |
|---|---|---|
| 4,258,058 A | 3/1981 | Witte et al. |
| 4,416,896 A | 11/1983 | Nakane et al. |
| 4,443,477 A | 4/1984 | Witte et al. |
| 4,663,336 A | 5/1987 | Nakane et al. |
| 4,752,616 A | 6/1988 | Hall et al. |
| 4,839,384 A | 6/1989 | Ogletree |
| 4,977,174 A | 12/1990 | Stein et al. |
| 5,066,480 A | 11/1991 | Ogletree et al. |
| 5,100,889 A | 3/1992 | Misra et al. |
| 5,128,359 A | 7/1992 | Bru-Magniez et al. |
| 5,312,818 A | 5/1994 | Rubin et al. |
| 5,399,725 A | 3/1995 | Poss et al. |
| 5,506,248 A | 4/1996 | Nikfar et al. |
| 6,509,348 B1 | 1/2003 | Ogletree |
| 7,785,891 B2 | 8/2010 | Phillips et al. |
| 8,299,097 B2 | 10/2012 | Boyce |
| 2006/0009496 A1 | 1/2006 | Dates et al. |
| 2009/0012115 A1 | 1/2009 | Phillips et al. |
| 2009/0012136 A1 | 1/2009 | Stephens et al. |
| 2009/0022729 A1 | 1/2009 | Mackman et al. |

FOREIGN PATENT DOCUMENTS

| | | |
|---|---|---|
| EP | 0337697 A2 | 10/1989 |
| EP | 0638310 A1 | 2/1995 |
| JP | H02273625 A | 11/1990 |

(Continued)

OTHER PUBLICATIONS

Acquaviva, A., et al., "Signaling pathways involved in isoprostane-mediated fibrogenic effects in rat hepatic stellate cells" Free Radical Biology and Medicine, vol. 65, pp. 201-207 (2013).

Amrstrong, R. et al., Competitive antagonism at thromboxane receptors in human platelets, Brit. J. Pharmacol. 84(3):595-607 (1985).

Angeli, P., et al. "Reversal of type 1 hepatorenal syndrome with the administration of midodrine and octreotide." Hepatology. Jun. 1999;29(6):1690-7.

(Continued)

*Primary Examiner* — Shirley V Gembeh
(74) *Attorney, Agent, or Firm* — VIVICAR Law PLLC

(57) ABSTRACT

The present invention is directed to methods of treating, preventing, and/or ameliorating fibrosis syndrome, and in particular cardiac fibrosis, by administration of a therapeutically effective amount of ifetroban, or a pharmaceutically acceptable salt thereof.

10 Claims, No Drawings

(56) References Cited

FOREIGN PATENT DOCUMENTS

| WO | 2006132460 A1 | 12/2006 |
|---|---|---|
| WO | 2008137793 A1 | 11/2008 |
| WO | 2012009545 A1 | 1/2012 |

OTHER PUBLICATIONS

Bianchetti, A. et al., Pharmacological Actions of Levallorphan Allyl Bromide (CM 32191), A New Peripheral Narcotic Antagonist, Life Sci. 31, pp. 2261-2264, (1982).
Borgdorff, MA et al., "Sildenafil treatment in established right ventricular dysfunction improves diastolic function and attenuates interstitial fibrosis independent from afterload" Am J Physiol Heart Circ Physiol 307, pp. H361-H369 (2014).
Bresnahan, B., et al. "Mesangial Cell Immune Injury" J. Amer. Society of Nephrology, 1991, pp. 1041-1047.
Brittain, R.T. et al., "AH 23848: A Thromboxane Receptor-Blocking drug that can Clarify the Pathophysiologic Role of Thromboxane A2," Circulation 72(6):1208-1218 (1985).
Bruggeman, L.A., et al. "Thromboxane stimulates synthesis of extracellular matrix proteins in vitro" Am. J. Physiol. 261, F488-F494 (1991).
Byland, E. et al., "ICI 185282: A Selective, Potent Thromboxane A2 Receptor Antagonist on Smooth Muscle," Brit. J. Pharmacol. 90 (Proc. Suppl):228 P-Abs, (1985).
Cathcart et al. "Cyclooxygenase-2—linked attenuation of hypoxia—induced pulmonary hypertension and intravascular thrombosis", The Journal of Pharmacology and Experimental Therapeutics, vol. 326, No. 1, pp. 51-58 (2008).
Cediel, E., et al. "AT-1 receptor antagonism modifies the mediation of endothelin-1, thromboxane A2, and catecholamines in the renal constrictor response to angiotensin II," Kidney International (2005) 67, pp. 1-10.
Cediel, et al., AT-1 receptor antagonism modifies the mediation of endothelin-1, thromboxane A2, and catecholamines in the renal constrictor response to angiotensin II, 2005, Kidney International, vol. 67, pp. S3-S9.
Comporti, M. et al. "F2-isoprostanes stimulate collagen synthesis in activated hepatic stellate cells: a link with liver fibrosis?" Laboratory Investigation, vol. 85, pp. 1381-1391, (2005).
Dockens, R., et al., "Disposition of Radiolabeled Ifetroban in Rats, Dogs, Monkeys, and Humans," Drug Metabolism and Disposition, 2000, vol. 28 No. 8; pp. 973-980.
Dogan et al. "Thromboxane A_2 Receptor Mediation of Calcium and Calcium Transients in Rat Cardiomyocytes" Life Sciences; Elsevier; vol. 60, No. 12, pp. 943-952 (1997).
Dogne, J-M., et al., "Recent developments of thromboxane modulators," Exp. Opin. Ther. Patents 11: 1663-1675 (2001).
Donovan, JP., et al. "Cerebral edema and increased intracranial pressure in chronic liver disease." Lancet. 1998;351 (9104):719-21.
Dr. G. Wright, "Hepatic Encephalopathy; The role of Inflammation, Ammonia and Aquaporin Expression in the Pathogenesis of Cerebral Oedema," Liver failure group, The Institute of Hepatology, University College London, Sep. 2009, pp. 1-292.
European Search Report from corresponding European Patent Application No. EP 15792047 dated Nov. 9, 2017.
Fanelli, F., et al. "Management of refractory hepatic encephalopathy after insertion of TIPS: long-term results of shunt reduction with hourglass-shaped balloon-expandable stent-graft." Am J Roentgenol. Dec. 2009;193(6):1696-702.
Fevery J, et al., "Reversal of hepatorenal syndrome in four patients by peroral misoprostol (prostaglandin E1 analogue) and albumin administration," J Hepatol. 11(2):153-8 (1990).
Ford-Hutchinson, A.W., et al. "The pharmacology of L-670,596," Can. J. Physiol. Pharmacol., 1989, 67:989-993.
Francois et al. "A role for the thromboxane receptor in L-NAME hypertension" Am. J. Physiol. Renal. Physiol., vol. 295, pp. 1096-1102 (2008).
Francois et al. "Prostacyclin protects against elevated blood pressure and cardiac fibrosis", Cell Metabolism, vol. 2, No. 3, pp. 201-207 (2005).
Francois et al. "Role for Thromboxane Receptors Angiotensin-II—Induced Hypertension" Hypertension, 43:364-369 (2004).
Gardi, C. et al. "F2-isoprotane receptors on hepatic stellate cells" Laboratory Investigation, vol. 88, pp. 124-131 (2007).
Gelosa, P., et al. "Terutroban, a thromboxane/prostaglandin endoperoxide receptor antagonist, prevents hypertensive vascular hypertrophy and fibrosis" Am J Physiol Heart Circ Physiol 300: pp. H762-H768 (2010).
Gentilini, P., et al. "Renal effects of a thromboxane (TX) A2 receptor antagonist (ONO-3708) in cirrhotics with ascites (C)," Journal of Hepatology, vol. 11, Jan. 1, 1990, p. S25.
Gluud, L.L., et al. "Systematic review of randomized trials on vasoconstrictor drugs for hepatorenal syndrome." Hepatology. 2010 51:576-584.
Grandi, AM et al., "Aldosterone Antagonist Improves Diastolic Function in Essential Hypertension" Hypertension 40, pp. 647-652 (2002).
Guevara M, et al. "Hepatorenal syndrome," Dig Dis. 2005;23(1):47-55.
Guevara M., et al., "Hepatorenal syndrome." Int J Biochem Cell Biol. Jan. 2005;37(1):22-6.
Hall, R.A et al., "Pharmacology of L-655,240 (3-[1-(4-chlorobenzyl)-5-fluoro-3-methyl-indol-2-yl] 2,2-dimethylpropanoic acid); a potent, selective thromboxane / prostaglandin endoperoxide antagonist," Eur. J. Pharmacol. 135(2):193-201 (1987).
Hara et al. "Augmented Cardiac Hypertrophy in Response to Pressue Overload in Mice Lacking the Prostaglandin I_2 Receptor" Circulation, 112:84-92 (2005).
International Search Report in International Application No. PCT/US15/31395, dated Aug. 10, 2015.
Japanese Office Action from corresponding Japanese Patent Application No. 2017-512891 dated Aug. 29, 2017 (English Translation).
Japanese Office Action from corresponding Japanese Patent Application No. 2017-512891 dated Aug. 29, 2017.
Jessup, C.L. et al., "ICI 159995: A Novel Thromboxane A2 Receptor Antagonist," Brit. J. Pharmacol. 86 (Proc. Suppl):808 P-Abs., (1985).
Jiang, Q et al., "Cardiovascular Phamtacology Inhibitory effect of ginsenoside Rb1 on calcineurin signal pathway in cardiomyocyte hypertrophy induced by prostaglandin F2alpha" Acta Pharmacologica Sinica 28, p. 1149-1154 (2007).
Kramer, H.J., et al., "Effect of Thromboxane A2 Receptor Blockade on Oliguric Ischemic Acute Renal Failure in Conscious Rats," J. Am. Soc. Nephrol., 1993 vol. 4 No. 1, pp. 50-57.
Kunapuli, P. et al. "Prostaglandin F2alpha (PGF2alpha) and the Isoprostane, 8, 12-iso-Isoprostane F2alpha-III, Induce Cardiomyocyte Hypertrophy" The Journal of Biological Chemistry, vol. 273, No. 35, pp. 22442-22452, (1998).
Kurokawa, S., et al. "Effect of inhaled KP-496, a novel dual antagonist of the cysteinyl leukotriene and thromboxane A2 receptors, on a bleomycin-induced pulmonary fibrosis model in mice" Pulmonary Pharmacology & Therapeutics, vol. 23, pp. 425-431 (2010).
Lenz K, et al. "Beneficial effect of 8-ornithin vasopressin on renal dysfunction in decompensated cirrhosis," Gut. Jan. 1989;30(1):90-6.
Lenz K, et al. "Omnipressin in the treatment of functional renal failure in decompensated liver cirrhosis. Effects on renal hemodynamics and atrial natriuretic factor," Gastroenterology. Oct. 1991;101(4):1060-7.
Lenz K, et al., "Enhancement of renal function with ornipressin in a patient with decompensated cirrhosis," Gut, 1985;26(12):1385-6.
Liu, T, et al. "Prostaglandin E2 deficiency causes a phenotype of aspirin sensitivity that depends on platelets and cysteinyl leukotrienes" Proc Natl Acad Sci USA. (2013) Abstract only.
Liu, T., et al. "Prostaglandin E2 deficiency causes a phenotype of aspirin sensitivity that depends on platelets and cysteinyl leukotrienes" PNAS, Early Edition, pnas.org/cgi/doi/10.1073/pnas.1313185110 (2013).

(56) References Cited

OTHER PUBLICATIONS

Nanji, A. et al. "Thromboxane Inhibitors Attenuate Inflammatory and Fibrotic Changes in Rat Liver Despite Continued Ethanol Administrtions" Alcoholism: Clinical and Experimental Research, vol. 37, No. 1, pp. 31-39 (2013).

Nanji, A. et al. "Thromboxane Inhibitors Attenuate Pathological Changes in Alcoholic Liver Disease in the Rat" Gastroenterology, vol. 112, pp. 200-207 (1997).

Narisada, M et al., S-1452, Shionogi domitroban, Anboxan®. pp. 1-14 (2004).

Peters, et al., "Acute hepatic failure: limitations of medical treatment and indications for liver transplantation." The Clinical Investigator, 1993, vol. 71, No. 11, pp. 875-881.

Pidgeon et al. "Intravascular thrombosis after hypoxia-induced pulmonary hypertension—Regulation by cyclooxygenase-2", Circulation, American Heart Association Inc., vol. 110, No. 17, pp. 2701-2707 (2004).

Rosado, E. et al., "Terutroban, a TP-Receptor Antagonsist, Reduces Portal Pressure in Cirrhotic Rats" Hepatology, Official Journal of the American Association for the Study of Liver Diseases, pp. 1-12 (2013).

Rosenfeld, L., et al., "Ifetroban Sodium: An Effective TxA2/PGH2 Receptor Antagonist," Cardiovascular Drug Reviews, vol. 19, No. 2, pp. 97-115 (2001).

Soper CP, et al., "Amelioration of hepatorenal syndrome with selective endothelin-A antagonist," Lancet. Jun. 29, 1996;347(9018):1842-3.

Touchberry et al. "Cardiac Thromboxane A2 Receptor Activation Does Not Directly Induce Cardiomyocyte Hypertrophy but Does Cause Cell Death that is Prevented with Gentamicin and 2-APB" BMC Pharmacology and Toxicology, vol. 15, pp. 1-12 (2014).

Wacker et al. "Inhibition of Thromboxane $A_2$- Induced Arrhythmias and Intracellular Calcium Changes in Cardiac Myocytes by Blockade of the Inositol Trisphosphate Pathway" The Journal of Pharmacology and Experimental Therapeutics, vol. 331, No. 3, pp. 917-924 (2009).

Wasserman, et al. SKF 88046, Smith Kline & West Laboratories, Pharmacologist 25(3):116 Abs., 117 Abs, (Aug. 1983).

Zhang et al. "COX-2 Dependent Cardiac Failure in Gh/ITG Transgenic Mice" Circulation Research; Journal of the American Heart Association, vol. 92, pp. 1153-11612003).

Kizer et al. "Association Between Pulmonary Fibrosis and Coronary Artery Disease," Arch. Intern. Med., 164:551-556 (2004).

Kahan et al. "Cardiac complications of systemic sclerosis," Rheumatology (Oxford), 48 Suppl 3:iii45-8 (2009).

Scleroderma Foundation, "Pulmonary Fibrosis in Systemic Sclerosis," (2018).

Steen, et al. "Pulmonary arterial hypertension and severe pulmonary fibrosis in systemic sclerosis patients with a nucleolar antibody,"J Rheumatol, 34(11):2230-5 (2007).

Reilly, I.A.G. et al., "Biosynthesis of thromboxane in patients with systemic sclerosis and Raynaud's phenomenon," British Medical Journal. vol. 292:1037-1039 (1986).

Mathai, S.C., et al. "Pulmonary arterial hypertension associated with systemic sclerosis," Expert Rev. Respir. Med., 5(2):267-279 (2011).

COMPOSITIONS AND METHODS OF TREATING CARDIAC FIBROSIS WITH IFETROBAN

CROSS-REFERENCE TO RELATED APPLICATIONS

This application is a continuation of U.S. application Ser. No. 17/151,181, filed Jan. 17, 2021, which is a continuation of U.S. application Ser. No. 16/752,933, filed Jan. 27, 2020, which is a continuation of U.S. application Ser. No. 16/391,444, filed Apr. 23, 2019, now U.S. Pat. No. 10,583,126, which is a continuation of U.S. application Ser. No. 16/004,666, filed Jun. 11, 2018, now U.S. Pat. No. 10,314,824, which is a continuation of U.S. application Ser. No. 15/608,507, filed May 30, 2017, now U.S. Pat. No. 10,016,399, which is a continuation of U.S. application Ser. No. 14/715,143, filed May 18, 2015, now U.S. Pat. No. 9,693,998, which claims priority to and the benefit of U.S. Patent Application Ser. No. 62/118,896, filed Feb. 20, 2015, U.S. Patent Application Ser. No. 62/078,649, filed Nov. 12, 2014, and U.S. Patent Application Ser. No. 61/994,436, filed on May 16, 2014, all of which are hereby incorporated by reference in their entirety.

STATEMENT REGARDING FEDERALLY SPONSORED RESEARCH OR DEVELOPMENT

This invention was made with government support under grant number P01HL108800 awarded by the National Institutes of Health. The government has certain rights in the invention.

FIELD OF THE INVENTION

The present invention is related to the use of thromboxane $A_2$ receptor antagonists (e.g., ifetroban) in the treatment and/or prevention of fibrosis in mammals, e.g., humans, and pharmaceutical compositions for the same comprising thromboxane $A_2$ receptor antagonists (e.g., ifetroban) in an effective amount to treat and/or prevent these diseases. In certain embodiments, the fibrosis is cardiac fibrosis.

BACKGROUND OF THE INVENTION

Fibrosis is the formation of excess fibrous connective tissue in an organ or tissue in a reparative or reactive process. This can be a reactive, benign, or pathological state, and physiologically acts to deposit connective tissue, which can obliterate the architecture and function of the underlying organ or tissue. Fibrosis can be used to describe the pathological state of excess deposition of fibrous tissue, as well as the process of connective tissue deposition in healing. While the formation of fibrous tissue is normal, and fibrous tissue is a normal constituent of organs or tissues in the body, scarring caused by a fibrotic condition may obliterate the architecture of the underlying organ or tissue.

For example, as fibrotic scar tissue replaces heart muscle damaged by hypertension, the heart becomes less elastic and thus less able to do its job. Similarly, pulmonary fibrosis causes the lungs to stiffen and impairs lung function. Fibrotic growth can proliferate and invade healthy surrounding tissue, even after the original injury heals. In most cases fibrosis is a reactive process, and several different factors can apparently modulate the pathways leading to tissue fibrosis. Such factors include the early inflammatory responses, local increase in fibroblast cell populations, modulation of the synthetic function of fibroblasts, and altered regulation of the biosynthesis and degradation of collagen. Other factors include inflammation of the nearby tissue, or a generalized inflammatory state, with increased circulating mediators.

Fibrosis includes pathological conditions characterized by abnormal and/or excessive accumulation of fibrotic material (e.g., extracellular matrix) following tissue damage. Fibroproliferative disease is responsible for morbidity and mortality associated with vascular diseases, such as cardiac disease, cerebral disease, and peripheral vascular disease, and with organ failure in a variety of chronic diseases affecting the pulmonary system, renal system, eyes, cardiac system, hepatic system, digestive system, and skin.

To date, there are no commercially available therapies that are effective in treating or preventing fibrotic disease, particularly cardiac fibrosis. Conventional treatment of most fibrosis-related disorders frequently involves corticosteroids, such as prednisone, and/or other medications that suppress the body's immune system. The goal of current treatment regimens is to decrease inflammation and subsequent scarring. Responses to currently available treatments are variable, and the toxicity and side effects associated with these treatments can be serious. Indeed, only a minority of patients respond to corticosteroids alone, and immune suppression medications are often used in combination with corticosteroids.

Right ventricular (RV) failure is the primary cause of death in pulmonary arterial hypertension (PAH), and is a source of significant morbidity and mortality in other forms of pulmonary hypertension. Production of thromboxane and F2 isprostanes, both agonists of the thromboxane/prostainoid (TP) receptor, is increased in pathological states increasing load stress, such as pulmonary arterial hypertension. The prostacyclin/thromboxane balance has been associated with cardioprotective effects under stress, probably through support of the coronary arteries. While aspirin treatment can decrease both thromboxane and prostaglandin production, it will suppress beneficial prostacyclin production and has no effect on isoprostane formation.

There are no approved therapies directed at preserving RV function. F-series and E-series isoprostanes are increased in heart failure and PAH, correlate to the severity of disease, and can signal through the thromboxane/prostanoid (TP) receptor, with effects from vasoconstriction to fibrosis. Loss of RV function can progress despite treatments decreasing pulmonary arterial pressure. RV response to chronic pressure overload can take both adaptive and maladaptive forms, which often determines clinical outcome. Adaptive ventricular hypertrophy with increased protein synthesis sustains function, while fibrosis and cardiomyocyte hypertrophy can cause arrhythmias and contractile dysfunction, and maladaptive dilatation is associated with RV failure. Consequently, treatment strategies promoting adaptive hypertrophy in the face of chronic load stress could preserve cardiac function and improve outcomes.

The development of cellular hypertrophy and myocardial fibrosis that occurs with chronic pressure overload is also associated with increased oxidative stress and lipid peroxidation. The $15\text{-}F_{2t}$ isoprostane ($8\text{-isoPGF}_{2\alpha}$, or 8-isoF) is a common biomarker for oxidative stress, and its levels increase with ventricular dilatation and correlate with the severity of heart failure. In addition to being a biomarker, it is suggested that 8-isoF and other isoprostanes can play a direct role in cardiomyopathy. F-series and E-series isoprostanes are known to signal through the thromboxane/prostanoid (TP) receptor, with effects ranging from vasoconstriction to fibrosis. The cyclooxygenase (COX) products of cyclic endoperoxide ($PGH_2$) and thromboxane $A_2$ ($TxA_2$) are also ligands of the TP receptor, and TP receptor activation contributes to cardiac hypertrophy in models of chronic hypertension and decreases cardiac function in Gh-overexpressing mice. The TP receptor is found not only in platelets and vessels but also the right ventricle, where receptor density is increased in PAH patients.

SUMMARY OF THE INVENTION

It is an object of the present invention to provide new methods of preventing and/or treating fibrosis and/or sclerosis in mammals, e.g., humans.

It is an object of the present invention to provide a composition and method for preventing and/or treating and/or attenuating cardiac fibrosis in mammals, e.g., humans.

It is yet another object of the present invention to provide a composition and method for reducing the effects of cardiac fibrosis in mammals, e.g., humans.

It has now been unexpectedly discovered that treatment of a mammal with a therapeutically effective amount of a thromboxane $A_2$ receptor antagonist (e.g., ifetroban) can prevent or attenuate cardiac fibrosis and associated sequalae. In certain embodiments, the administration of the therapeutically effective amount of a thromboxane $A_2$ receptor antagonist (e.g., ifetroban) can prevent or attenuate cardiomyopathy and cardiac failure in situations of pressure overload from inflammation and fibrosis towards a functional physiologic hypertrophy.

In accordance with the above objects, the present invention provides for methods of preventing, reversing, ameliorating or treating fibrosis by administering a therapeutically effective amount of a thromboxane $A_2$ receptor antagonist (e.g., ifetroban or a pharmaceutically acceptable salt thereof (e.g., ifetroban sodium)) to a patient in need thereof.

In accordance with the above objects, the present invention provides for methods of preventing, reversing, ameliorating or treating cardiac fibrosis by administering a therapeutically effective amount of a thromboxane $A_2$ receptor antagonist (e.g., ifetroban) to a patient in need thereof.

In certain embodiments, the present invention is directed to a method of treating and/or ameliorating a fibrotic disease or condition in a patient, in particular cardiac fibrosis, comprising administering to a patient in need thereof a therapeutically effective amount of a thromboxane $A_2$ receptor antagonist to provide a desired plasma concentration of the thromboxane $A_2$ receptor antagonist (and/or its active metabolites) of about 0.1 ng/ml to about 100,000 ng/ml. In certain embodiments, the therapeutically effective amount of a thromboxane $A_2$ receptor antagonist to provide a desired plasma concentration of the thromboxane $A_2$ receptor antagonist of about 0.1 ng/ml to about 10,000 ng/ml. In certain preferred embodiments, the thromboxane $A_2$ receptor antagonist is ifetroban or a pharmaceutically acceptable salt thereof, e.g., ifetroban sodium.

The invention is also directed to a method of providing cardioprotective effects to a human patient(s) who is experiencing pulmonary arterial hypertension, via the administration of a thromboxane $A_2$ receptor antagonist as described herein.

The invention is further directed to a method of improving right heart adaptation to load stress in a human patient(s) via the administration of a thromboxane $A_2$ receptor antagonist as described herein.

In certain embodiments, the thromboxane $A_2$ receptor antagonist comprises a therapeutically effective amount of [1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid (Ifetroban), and pharmaceutically acceptable salts thereof.

The invention is further directed to a method of treating cardiac fibrosis in a mammal in need of treatment thereof, comprising administering a therapeutically effective amount of [1S-(1α,2α,3α,4 α)]-2-[[3-[4-[(Pentylamino)carbonyl]-2-oxazolyl]-7-oxabicyclo[2.2.1]hept-2-yl]methyl]-benzenepropanoic acid (ifetroban), or a pharmaceutically acceptable salt thereof to the mammal. In certain embodiments, the thromboxane $A_2$ receptor antagonist comprises a therapeutically effective amount of [1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid, monosodium salt (Ifetroban Sodium). In certain preferred embodiments, the therapeutically effective amount of ifetroban reduces the rate of formation of fibrotic tissue in the mammal. In certain preferred embodiments, the mammal is a human patient. In certain preferred embodiments, the therapeutically effective amount of ifetroban slows the progression of myocardial fibrosis in the human patient and/or improves the exercise capacity in the human patient and/or reduces RV fibrosis in the human patient, and/or reduces cardiomyocyte hypertrophy in the human patient, and/or provides an increased E/A ratio in the human patient, and/or increases cardiomyocyte diameter in the human patient, and/or improves or maintains a function selected from the group consisting of right ventricular ejection fraction (RVEF), left ventricular ejection fraction (LVEF), pulmonary dynamics, right ventricular systolic pressure (RVSP), left ventricular systolic function (LVSF), right ventricular diastolic function (RVDF), and left ventricular diastolic function (LVDF).

In certain preferred embodiments, the therapeutically effective amount of ifetroban is cardioprotective against pressure overload, by moving the right heart towards adaptation rather than a maladaptive fibrosis, inflammation and cellular hypertrophy.

In certain preferred embodiments, the therapeutically effective amount of ifetroban attenuates left heart failure in the human patient.

In any of the methods described above and others described herein, the ifetroban is preferably administered in an amount effective to provide a plasma concentration of the ifetroban (and/or active metabolites of ifetroban) of about 1 ng/ml to about 100,000 ng/ml or of about 1 ng/ml to about 10,000 ng/ml for ifetroban itself, and in some embodiments from about 1 ng/ml to about 1,000 ng/ml. In some embodiments, the afore-mentioned plasma concentration is a plasma concentration at steady state. In some embodiments, the afore-mentioned plasma concentration is a maximum plasma concentration (Cmax). In certain preferred embodiments where the mammal is a human patient, the therapeutically effective amount is from about 100 mg to about 2000 mg per day, or from about 10 mg or about 100 mg to about 1000 mg per day, and certain embodiments more preferably from about 100 to about 500 mg per day. The daily dose may be administered in divided doses or in one bolus or unit dose or in multiple dosages administered concurrently. In this regard, the ifetroban may be administered orally, intranasally, rectally, vaginally, sublingually, buccally, parenterally, or transdermally.

The invention is further directed to a pharmaceutical composition comprising a thromboxane $A_2$ receptor antagonist (e.g., ifetroban or a pharmaceutically acceptable salt thereof), the thromboxane $A_2$ receptor antagonist being in an amount effective to improve or maintain a function selected from the group consisting of right ventricular ejection fraction (RVEF), left ventricular ejection fraction (LVEF), pulmonary dynamics, right ventricular systolic pressure (RVSP), left ventricular systolic function (LVSF), right ventricular diastolic function (RVDF), and left ventricular diastolic function (LVDF) in a mammal in need thereof. In certain preferred embodiments, the ifetroban salt is ifetroban sodium.

In certain preferred embodiments, the pharmaceutical composition described above, the therapeutically effective amount is from about 10 mg to about 1000 mg ifetroban per day. In certain preferred embodiments, the therapeutically effective amount is from about 100 to about 500 mg per day.

The present invention also relates to methods and compositions for treating fibrosis in a subject(s) or patient(s) in need of treatment thereof, particularly, cardiac fibrosis, the method comprising administering a therapeutically effective amount of a thromboxane $A_2$ receptor antagonist to a subject(s) or patient(s) in need thereof. In particular, it relates to a method of treating or preventing a disorder that results in fibrosis or sclerosis, in a subject(s) or patient(s) in need of such treatment, comprising administering a composition comprising administering a therapeutically effective amount of a thromboxane $A_2$ receptor antagonist to a patient in need thereof in an amount effective to reduce the rate of fibrosis or sclerosis. Further provided is a method of preventing fibrosis or sclerosis in a subject(s) or patient(s) in need of such treatment, comprising administering a composition comprising a thromboxane $A_2$ receptor antagonist in an amount effective to reduce the formation of fibrotic or sclerotic tissue that would occur in the absence of such treatment.

In a certain embodiment, the fibrosis is associated with a fibroproliferative disease selected from the group consisting of heart fibrosis, kidney fibrosis, liver fibrosis, lung fibrosis, and systemic sclerosis.

DETAILED DESCRIPTION OF THE INVENTION

In accordance with the above stated objects, it is believed that administration of a therapeutically effective amount of a thromboxane $A_2$ receptor antagonist to a subject(s) or patient(s) in need thereof can prevent and/or treat fibrosis (fibrotic diseases or conditions, and in particular, cardiac fibrosis).

Failure of the right ventricle to adapt to load stress is the direct cause of mortality in pulmonary arterial hypertension. Thromboxane production is increased in pathological states increasing load stress such as pulmonary arterial hypertension, and the prostacyclin/thromboxane balance has been associated with cardioprotective effects under stress, probably through support of the coronary arteries. While aspirin treatment can decrease both thromboxane and prostaglandin production, it also suppresses beneficial prostacyclin production and a more targeted approach may be necessary.

Fibrosis can occur in many tissues within the body, typically as a result of inflammation or damage, and examples include: Pulmonary fibrosis (lungs); Idiopathic pulmonary fibrosis (where the cause is unknown); cystic fibrosis; liver fibrosis or cirrhosis (liver); heart fibrosis, including endomyocardial fibrosis (heart), old myocardial infarction (heart), atrial fibrosis (heart); and other fibrotic conditions including but not limited to mediastinal fibrosis (soft tissue of the mediastinum), myelofibrosis (bone marrow), retroperitoneal fibrosis (soft tissue of the retroperitoneum), progressive massive fibrosis (lungs); a complication of coal workers' pneumoconiosis, nephrogenic systemic fibrosis (skin), Crohn's Disease (intestine), keloid (skin), scleroderma/systemic sclerosis (skin, lungs), arthrofibrosis (knee, shoulder, other joints), and some forms of adhesive capsulitis (shoulder). Other names for various types of pulmonary fibrosis that have been used in the past include chronic interstitial pneumonitis, Hamman-Rich Syndrome, usual interstitial pneumonitis (UIP) and diffuse fibrosing alveolitis.

Symptoms of pulmonary fibrosis include shortness of breath, cough, and diminished exercise tolerance. The severity of symptoms and the worsening of symptoms over time can vary and are at least partially dependent upon the cause of the fibrosis.

Cirrhosis is extensive scarring (fibrosis) in the liver caused by long-term damage. This damage is caused by inflammation, which is a normal response to some injuries like chronic viral infection or chronic alcoholism. The liver repairs the damaged areas by replacing them with scar tissue, in similar fashion to scar tissue developing during the healing process when a subject sustains a cut on their body. Fibrosis in the liver is different from the surrounding healthy liver tissue. Unfortunately, since scar tissue can't function as normal hepatocytes, too much scar tissue interferes with essential liver functions. Cirrhosis has many causes, but the most common is alcoholism and chronic hepatitis. Some of the other causes of cirrhosis are obstructed bile ducts in the liver and gallbladder, autoimmune hepatitis, and inherited diseases like Wilson's disease or hemochromatosis.

Liver fibrosis is a scarring process initiated in response to chronic liver disease (CLD) caused by continuous and repeated insults to the liver. Later stages of CLD are characterized by extensive remodeling of the liver architecture and chronic organ failure, regardless of the underlying disease (e.g., cirrhosis, nonalcoholic steatohepatitis (NASH), primary sclerosing cholangitis (PSC)).

Idiopathic pulmonary fibrosis (IPF) is the main form of lung fibrosis. IPF is a debilitating and life-threatening lung disease characterized by a progressive scarring of the lungs that hinders oxygen uptake.

Systemic sclerosis is a degenerative disorder in which excessive fibrosis occurs in multiple organ systems, including the skin, blood vessels, heart, lungs, and kidneys. Several forms of fibrotic diseases cause death in scleroderma patients, including pulmonary fibrosis, congestive heart failure, and renal fibrosis; each of which occurs in about half of systemic sclerosis patients.

Fibrosis is also a leading cause of organ transplant rejection.

The phrase "therapeutically effective amount" refers to that amount of a substance that produces some desired local or systemic effect at a reasonable benefit/risk ratio applicable to any treatment. The effective amount of such substance will vary depending upon the subject and disease condition being treated, the weight and age of the subject, the severity of the disease condition, the manner of administration and the like, which can readily be determined by one of ordinary skill in the art.

The term "thromboxane A2 receptor antagonist" as used herein refers to a compound that inhibits the expression or activity of a thromboxane receptor by at least or at least about 30%, 35%, 40%, 45%, 50%, 55%, 60%, 65%, 70%, 75%, 80%, 85%, 90%, 95%, 96%, 97%, 98%, 99%, or 100% in a standard bioassay or in vivo or when used in a therapeutically effective dose. In certain embodiments, a thromboxane A2 receptor antagonist inhibits binding of thromboxane $A_2$ to the receptor. Thromboxane A2 receptor antagonists include competitive antagonists (i.e., antagonists that compete with an agonist for the receptor) and non-competitive antagonists. Thromboxane A2 receptor antagonists include antibodies to the receptor. The antibodies may be monoclonal. They may be human or humanized antibodies. Thromboxane A2 receptor antagonists also include thromboxane synthase inhibitors, as well as compounds that have both thromboxane A2 receptor antagonist activity and thromboxane synthase inhibitor activity.

Thromboxane $A_2$ Receptor Antagonist

The discovery and development of thromboxane $A_2$ receptor antagonists has been an objective of many pharmaceutical companies for approximately 30 years (see, Dogne J-M, et al., Exp. Opin. Ther. Patents 11: 1663-1675 (2001)). Certain individual compounds identified by these companies, either with or without concomitant thromboxane $A_2$ synthase inhibitory activity, include ifetroban (BMS), ridogrel (Janssen), terbogrel (BI), UK-147535 (Pfizer), GR 32191 (Glaxo), and S-18886 (Servier). Preclinical pharmacology has established that this class of compounds has effective antithrombotic activity obtained by inhibition of the thromboxane pathway. These compounds also prevent vasoconstriction induced by thromboxane $A_2$ and other prostanoids that act on the thromboxane $A_2$ receptor within the vascular bed, and thus may be beneficial for use in preventing and/or treating hepatorenal syndrome and/or hepatic encephalopathy.

Suitable thromboxane A2 receptor antagonists for use in the present invention may include, for example, but are not limited to small molecules such as ifetroban (BMS; [1S-(1α,2α,3α,4α)]-2-[[3-[4-[(pentylamino)carbonyl-1]-2-oxazolyl]-7-oxabicyclo[2.2.1]hept-2 yl]methyl]benzenepropanoic acid), as well as others described in U.S. Patent Application Publication No. 2009/0012115, the disclosure of which is hereby incorporated by reference in its entirety.

Additional thromboxane A2 receptor antagonists suitable for use herein are also described in U.S. Pat. No. 4,839,384 (Ogletree); U.S. Pat. No. 5,066,480 (Ogletree, et al.); U.S. Pat. No. 5,100,889 (Misra, et al.); U.S. Pat. No. 5,312,818 (Rubin, et al.); U.S. Pat. No. 5,399,725 (Poss, et al.); and U.S. Pat. No. 6,509,348 (Ogletree), the disclosures of which are hereby incorporated by reference in their entireties. These may include, but are not limited to, interphenylene 7-oxabicyclo-heptyl substituted heterocyclic amide prostaglandin analogs as disclosed in U.S. Pat. No. 5,100,889, including:

[1S-(1α, 2α, 3α, 4α)]-2-[[3-[4-[[(4-cyclo-hexylbutyl)amino]carbonyl]-2-oxazolyl]-7-oxabicyclo[2.2.1]-hept-2-yl]methyl]benzenepropanoic acid (SQ 33,961), or esters or salts thereof;

[1S-(1α, 2α, 3α, 4α)]-2-[[3-[4-[[[(4-chloro-phenyl)-butyl]amino]carbonyl]-2-oxazolyl]-7-oxabicyclo[2.2.1]hept-2-yl]methyl]benzenepropanoic acid or esters, or salts thereof;

[1S-(1α, 2α, 3α, 4α)]-3-[[3-[4-[[(4-cycloh-exylbutyl)-amino]carbonyl]-2-oxazolyl]-7-oxabicyclo[2.2.1]hept-2-yl]benzene acetic acid, or esters or salts thereof;

[1S-(1α, 2α, 3α, 4α)]-2-[[3-[4-[[(4-cyclohexyl-butyl)amino]carbonyl]-2-oxazolyl]-7-oxabicyclo[2.2.1]hept-2-yl]methyl]phenoxy]acetic acid, or esters or salts thereof;

[1S-(1α, 2α, 3α, 4α]-2-[[3-[4-[[(7,7-dime-thyloctyl)amino]carbonyl]-2-oxazolyl]-7-oxabicyclo[2.2.1]hept-2-yl]-methyl]benzenepropanoic acid, or esters or salts thereof.

7-oxabicycloheptyl substituted heterocyclic amide prostaglandin analogs as disclosed in U.S. Pat. No. 5,100,889, issued Mar. 31, 1992, including [1S-[1α, 2α(Z), 3α, 4α)]-6-[3-[4-[[(4-cyclohexylbutyl)amino]-carbonyl]-2-oxazolyl]-7-oxabicyclo[2.2.1]hept-2-yl]-4-hexenoic acid, or esters or salts thereof;

[1S-[1α, 2α (Z), 3α, 4α)]]-6-[3-[4-[[(4-cyclohexyl-butyl)amino]carbonyl]-2-thiazolyl]-7-oxabicyclo[2.2.1]hept-2-yl]-4-hexenoic acid, or esters or salts thereof;

[1S-[1α, 2α (Z), 3α, 4α)]]-6-[3-[4-[[(4-cyclohexyl-butyl)methylamino]carbonyl]-2-oxazolyl]-7-oxabicyclo-[2.2.1]hept-2-yl]-4-hexenoic acid, or esters or salts thereof;

[1S-[1α, 2α (Z), 3α, 4α)]]-6-[3-[4-[(1-pyrrolidinyl)-carbonyl]-2-oxazolyl]-7-oxabicyclo[2.2.1]hept-2-yl]-4-hexenoic acid, or esters or salts thereof;

[1S-[1α, 2α (Z), 3α, 4α)]]-6-[3-[4-[(cyclohexylamino)-carbonyl]-2-oxazolyl]-7-oxabicyclo[2.2.1]hept-2-yl-4-hexenoic acid or esters or salts thereof;

[1S-[1α, 2α (Z), 3α, 4α)]]-6-[3-[4-[[(2-cyclohexyl-ethyl)amino]carbonyl]-2-oxazolyl]-7-oxabicyclo[2.2.1]hept-2-yl]-4-hexenoic acid, or esters or salts thereof;

[1S-[1α, 2α (Z), 3α, 4 α)]]-6-[3-[4-[[[2-(4-chloro-phenyl)ethyl]amino]carbonyl]-2-oxazolyl]-7-oxabicyclo-[2.2.1]hept-2-yl]-4-hexenoic acid, or esters or salts thereof;

[1S-[1α, 2α (Z), 3α, 4α)]-6-[3-[4-[[(4-chlorophenyl)-amino]carbonyl]-2-oxazolyl]-7-oxabicyclo[2.2.1]hept-2-yl]-4-hexenoic acid, or esters or salts thereof;

[1S-[1α, 2α (Z), 3α, 4α)]]-6-[3-[4-[[[4-(4-chloro-phenyl)butyl]amino]carbonyl]-2-oxazolyl]-7-oxabicyclo-[2.2.1]hept-2-yl]-4-hexenoic acid, or esters or salts thereof;

[1S-[11α, 2α (Z), 3α, 4α)]]-6-[3-[4.alpha.-[[-(6-cyclohexylhexyl)amino]carbonyl]-2-oxazolyl]-7-oxabicyclo[2.2.1]hept-2-yl]-4-hexenoic acid, or esters, or salts thereof;

[1S-[1α, 2α (Z), 3α, 4α)]]-6-[3-[4-[[(6-cyclohexyl-hexyl)amino]carbonyl]-2-oxazolyl]-7-oxabicyclo[2.2.1]hept-2-yl]-4-hexenoic acid, or esters or salts thereof;

[1S-[1α, 2α (Z), 3α, 4α)]]-6-[3-[4-[(propylamino)-carbonyl]-2-oxazolyl]-7-oxabicyclo[2.2.1]hept-2-yl]-4-hexenoic acid, or esters or salts thereof

[1S-[1α, 2α (Z), 3α, 4α)]]-6-[3-[4-[[(4-butylphenyl)-amino]carbonyl]-2-oxazolyl]-7-oxabicyclo[2.2.1]hept-2-yl]-4-hexenoic acid, or esters or salts thereof;

[1S-[1α, 2α (Z), 3α, 4α)]]-6-[3-[4-[(2,3-dihydro-1H-indol-1-yl)carbonyl]-2-oxazolyl]-7-oxabicyclo (2.2.1]hept-2-yl]-4-hexenoic acid, or esters or salts thereof;

[1S-[1α, 2α (Z), 3α, 4α)]]-6-[3-[4-[[(4-cyclohexyl-butyl)amino]carbonyl]-2-oxazolyl]-7-oxabicyclo[2.2.1]hept-2-yl]-N-(phenylsulfonyl)-4-hexenamide;

[1S-[11α, 2α (Z), 3α, 4α)]]-6-[3-[4-[[(4-cyclohexyl-butyl)amino]carbonyl]-2-oxazolyl]-N-(methylsulfonyl)-7-oxabicyclo[2-.2.1]hept-2-yl]-4-hexenamide;

[1S-[1α, 2α (Z), 3α, 4α)]]-7-[3-[4-[[(4-cyclohexyl-butyl)amino]carbonyl]-2-oxazolyl]-7-oxabicyclo (2.2.1]hept-2-yl]-5-heptenoic acid, or esters or salts thereof;

[1S-[1α, 2α (Z), 3α, 4α)]]-6-[3-[4-[[(4-cyclohexyl-butyl)amino]carbonyl]-1H-imidazol-2-yl]-7-oxabicyclo-[2.2.1]hept-2-yl]-4-hexenoic acid or esters or salts thereof;

[1S-[1α, 2α, 3α, 4α)]-6-[3-[4-[[(7, 7-dimethyloctyl)-amino]carbonyl]-2-oxazolyl]-7-oxabicyclo[2.2.1]hept-2-yl]-4-hexenoic acid, or esters or salts thereof;

[1S-[1α, 2α(E), 3α, 4α)]]-6-[3-[4-[[(4-cyclohexyl-butyl)amino]carbonyl]-2-oxazolyl]-7-oxabicyclo[2.2.1]hept-2-yl]-4-hexenoic acid;

[1S-[1α, 2α, 3α, 4α)]-3-[4-[[(4-(cyclohexylbutyl)-amino]carbonyl]-2-oxazolyl]-7-oxabicyclo[2.2.1]heptane-2-hexanoic acid or esters or salts thereof,

[1S-[1α, 2α(Z), 3α, 4α)]]-6-[3-[4-[[(4-cyclohexyl-butyl) amino]carbonyl]-2-oxazolyl]-7-oxabicyclo-[2.2.1]hept-2-yl]-4-hexenoic acid, or esters or salts thereof;

7-oxabicycloheptane and 7-oxabicycloheptene compounds disclosed in U.S. Pat. No. 4,537,981 to Snitman et al, the disclosure of which is hereby incorporated by reference in its entirety, such as [1S-(1α, 2α(Z), 3 α(1E, 3S*, 4R*), 4 α)]]-7-[3-(3-hydroxy-4-phenyl-1-pentenyl)-7-oxabicyclo [2.2.1]hept-2-yl]-5-heptenoic acid (SQ 29,548); the 7-oxabicycloheptane substituted aminoprostaglandin analogs disclosed in U.S. Pat. No. 4,416,896 to Nakane et al, the disclosure of which is hereby incorporated by reference in its entirety, such as [1S-[1α, 2α(Z), 3α, 4α)]]-7-[3-[[2-(phenylamino)carbonyl]-hydrazino]methyl]-7-oxabicyclo[2.2.1]hept-2-yl]-5-heptenoic acid; the 7-oxabicycloheptane substituted diamide prostaglandin analogs disclosed in U.S. Pat. No. 4,663,336 to Nakane et al, the disclosure of which is hereby incorporated by reference in its entirety, such as, [1S-[1α, 2α(Z), 3α, 4α)]]-7-[3-[[[[(1-oxoheptyl)amino]-acetyl]amino]methyl]-7-oxabicyclo [2.2.1]hept-2-yl]-5-heptenoic acid and the corresponding tetrazole, and [1S-[1α, 2α(Z), 3α,4 α)]]-7-[3-[[[[(4-cyclohexyl-1-oxobutyl)-amino]acetyl]amino]methyl]-7-oxabicyclo]2.2.1]hept-2-yl]-5-heptenoic acid;

7-oxabicycloheptane imidazole prostaglandin analogs as disclosed in U.S. Pat. No. 4,977,174, the disclosure of which is hereby incorporated by reference in its entirety, such as [1S-[1α, 2α(Z), 3α, 4 α)]]-6-[3-[[4-(4-cyclohexyl-1-hydroxybutyl)-1H-imidazole-1-yl]methyl]-7-oxabicyclo[2.2.1]hept-2-yl]-4-hexenoic acid or its methyl ester;

[1S-[1α, 2α(Z), 3α, 4 α)]]-6-[3-[[4-(3-cyclohexyl-propyl)-1H-imidazol-1-yl]methyl]-7-oxabicyclo[2.2.1]hept-2-yl]-4-hexenoic acid or its methyl ester;

[1S-[1α, 2α(X(Z), 3α, 4α)]]-6-[3-[[4-(4-cyclohexyl-1-oxobutyl)-1H-imidazol-1-yl]methyl]-7-oxabicyclo[2.2.1] hept-2-yl]-4-hexenoic acid or its methyl ester;

[1S-[1α, 2α(Z), 3α, 4α]]-6-[3-(1H-imidazol-1-ylmethyl)-7-oxabicyclo[2.2.1]hept-2-yl]-4-hexenoic acid or its methyl ester; or

[1S-[1α, 2α(Z), 3α, 4α)]]-6-[3-[[4-[[(4-cyclohexyl-butyl) amino]carbonyl]-1H-imidazol-1-yl]methyl-7-oxabicyclo-[2.2.1]-hept-2-yl]-4-hexenoic acid, or its methyl ester;

The phenoxyalkyl carboxylic acids disclosed in U.S. Pat. No. 4,258,058 to Witte et al, the disclosure of which is hereby incorporated by reference in its entirety, including 4-[2-(benzenesulfamido)ethyl]phenoxy-acetic acid (BM 13,177-Boehringer Mannheim), the sulphonamidophenyl carboxylic acids disclosed in U.S. Pat. No. 4,443,477 to Witte et al, the disclosure of which is hereby incorporated by reference in its entirety, including 4-[2-(4-chlorobenzenesulfonamido)ethyl]-phenylacetic acid (BM 13,505, Boehringer Mannheim), the arylthioalkylphenyl carboxylic acids disclosed in U.S. Pat. No. 4,752,616, the disclosure of which is hereby incorporated by reference in its entirety, including 4-(3-((4-chlorophenyl)sulfonyl)propyl)benzene acetic acid.

Other examples of thromboxane $A_2$ receptor antagonists suitable for use herein include, but are not limited to vapiprost (which is a preferred example), (E)-5-[[[(pyridinyl)]3-(trifluoromethyl)phenyl]methylene]amino]-oxy]pentanoic acid also referred to as R68,070-Janssen Research Laboratories, 3-[1-(4-chlorophenylmethyl)-5-fluoro-3-methylindol-2-yl]-2,-2-dimethylpropanoic acid [(L-655240 Merck-Frosst) Eur. J. Pharmacol. 135(2):193, March 17, 87], 5(Z)-7-([2,4,5-cis]-4-(2-hydroxyphenyl)-2-trifl-uoromethyl-1,3-dioxan-5-yl)heptenoic acid (ICI 185282, Brit. J. Pharmacol. 90 (Proc. Suppl):228 P-Abs, March 87), 5(Z)-7-[2,2-dimethyl-4-phenyl-1,3-dioxan-cis-5-yl]heptenoic acid (ICI 159995, Brit. J. Pharmacol. 86 (Proc. Suppl):808 P-Abs., December 85), N,N'-bis[7-(3-chlorobenzeneaminosulfony-1)-1,2,3,4-tetrahydro-isoquinolyl]disulfonylimide (SKF 88046, Pharmacologist 25(3):116 Abs., 117 Abs, August 83), (1.alpha.(Z)-2.beta., 5.alpha.]-(+)-7-[5-[[(1,1'-biphenyl)-4-yl]-methoxy]-2-(4-morpholinyl)-3-oxocyclopentyl]-4-heptenoic acid (AH 23848-Glaxo, Circulation 72(6):1208, December 85, levallorphan allyl bromide (CM 32,191 Sanofi, Life Sci. 31 (20-21):2261, November 15, 82), (Z,2-endo-3-oxo)-7-(3-acetyl-2-bicyclo[2.2.1]heptyl-5-hepta-3Z-enoic acid, 4-phenyl-thiosemicarbazone (EP092-Univ. Edinburgh, Brit. J. Pharmacol. 84(3):595, March 85); GR 32,191 (Vapiprost)-[1R-[1.alpha.(Z), 2.beta., 3.beta., 5.alpha.]]-(+)-7-[5-([1,1'-biphenyl]-4-ylmethoxy)-3-hydroxy-2-(1-piperidinyl)cyclopentyl]-4-heptenoic acid; ICI 192,605-4(Z)-6-[(2,4,5-cis)2-(2-chlorophenyl)-4-(2-hydroxyphenyl)-1,3-dioxan-5-yl]hexenoic acid; BAY u 3405 (ramatroban)-3-[[(4-fluorophenyl)-sulfonyl]amino]-1,2,3,4-tetrahydro-9H-c-arbazole-9-propanoic acid; or ONO 3708-7-[2.alpha., 4.alpha.-(dimethylmethano)-6.beta.-(2-cyclopentyl-2.beta.-hydroxyacetami-do)-1.alpha.-cyclohexyl]-5 (Z)-heptenoic acid; (.+-.)(5Z)-7-[3-endo-((phenylsulfonyl) amino]-bicyclo[2.2.1]hept-2-exo-yl]-heptenoic acid (S-1452, Shionogi domitroban, Anboxan®); (−)6,8-difluoro-9-p-methylsulfonylben-zyl-1,2,3,4-tetrahydrocarbazol-1-yl-acetic acid (L670596, Merck) and (3-[1-(4-chlorobenzyl)-5-fluoro-3-methyl-indol-2-yl]-2,2-dimethylpropanoic acid (L655240, Merck).

The preferred thromboxane A2 receptor antagonist of the present invention is ifetroban or any pharmaceutically acceptable salts thereof.

In certain preferred embodiments the preferred thromboxane A2 receptor antagonist is ifetroban sodium (known chemically as [1S-(1α,2α,3α,4α)]-2-[[3-[4-[(Pentylamino) carbonyl]-2-oxazolyl]-7-oxabicyclo[2.2.1]hept-2-yl] methyl]-benzenepropanoic acid, monosodium salt.

Methods of Treatment

In certain embodiments of the present invention there is provided a method of preventing and/or treating and/or ameliorating fibrosis in one or more organs or tissues in a patient or patient population by administration of a therapeutically effective amount of a thromboxane $A_2$ receptor antagonist to a patient(s) in need thereof.

The administration of a therapeutically effective amount of a thromboxane $A_2$ receptor antagonist may be accomplished via any therapeutically useful route of administration, including but not limited to orally, intranasally, rectally, vaginally, sublingually, buccally, parenterally, or transdermally. In certain preferred embodiments, the thromboxane $A_2$ receptor antagonist is administered parenterally. In certain further embodiments, the thromboxane $A_2$ receptor antagonist is administered by intra-articular injection. In certain further embodiments, the thromboxane $A_2$ receptor antagonist is administered directly to the affected anatomic site. In another embodiment, the thromboxane $A_2$ receptor antagonist is administered through the hepatic artery.

In certain preferred embodiments, the plasma concentrations of thromboxane $A_2$ receptor antagonists range from about 0.1 ng/ml to about 10,000 ng/ml. Preferably, the plasma concentration of thromboxane $A_2$ receptor antagonists range from about 1 ng/ml to about 1,000 ng/ml.

When the thromboxane $A_2$ receptor antagonists is ifetroban, the desired plasma concentration for treatment or prevention of fibrosis in certain embodiments should be greater than about 10 ng/mL (ifetroban free acid). Some therapeutic effects of thromboxane $A_2$ receptor antagonist, e.g., ifetroban, may be seen at concentrations of greater than about 1 ng/mL.

The dose administered should be adjusted according to age, weight and condition of the patient, as well as the route of administration, dosage form and regimen and the desired result.

In order to obtain the desired plasma concentration of thromboxane $A_2$ receptor antagonists for the treatment or prevention of fibrosis, daily doses of the thromboxane $A_2$ receptor antagonists preferably range from about 0.1 mg to about 5000 mg. In certain preferred embodiments, the daily dose of thromboxane $A_2$ receptor antagonists for the treatment or prevention of fibrosis may range from about 1 mg to about 2000 mg; about 10 mg to about 1000 mg; from about 100 mg to about 1000 mg; from about 50 mg to about 500 mg; about 100 mg to about 500 mg; about 200 mg to about 500 mg; about 300 mg to about 500 mg; or from about 400 mg to about 500 mg per day.

In certain preferred embodiments, a daily dose of ifetroban sodium from about 10 mg to about 250 mg (ifetroban free acid amounts) will produce therapeutically effective plasma levels of ifetroban free acid for the treatment or prevention of fibrosis.

Preferably, the therapeutically effective plasma concentration of thromboxane $A_2$ receptor antagonists ranges from about 1 ng/ml to about 1,000 ng/ml for the treatment or prevention of fibrosis.

When the thromboxane $A_2$ receptor antagonist is ifetroban, the desired plasma concentration for providing an inhibitory effect of $A_2$/prostaglandin endoperoxide receptor (TPr) activation, and thus a reduction of cerebral microvascular activation should be greater than about 10 ng/mL (ifetroban free acid). Some inhibitory effects of thromboxane $A_2$ receptor antagonist, e.g., ifetroban, may be seen at concentrations of greater than about 1 ng/mL.

The dose administered must be carefully adjusted according to age, weight and condition of the patient, as well as the route of administration, dosage form and regimen and the desired result.

However, in order to obtain the desired plasma concentration of thromboxane $A_2$ receptor antagonists, daily doses of the thromboxane $A_2$ receptor antagonists ranging from about 0.1 mg to about 5000 mg should be administered. Preferably, the daily dose of thromboxane $A_2$ receptor antagonists ranges from about 1 mg to about 1000 mg; about 10 mg to about 1000 mg; about 50 mg to about 500 mg; about 100 mg to about 500 mg; about 200 mg to about 500 mg; about 300 mg to about 500 mg; and about 400 mg to about 500 mg per day.

In certain preferred embodiments, a daily dose of ifetroban sodium from about 10 mg to about 500 mg, preferably from about 10 mg to about 300 mg (ifetroban free acid amounts) will produce effective plasma levels of ifetroban free acid.

Pharmaceutical Compositions

The thromboxane $A_2$ receptor antagonists of the present invention may be administered by any pharmaceutically effective route. For example, the thromboxane $A_2$ receptor antagonists may be formulated in a manner such that they can be administered orally, intranasally, rectally, vaginally, sublingually, buccally, parenterally, or transdermally, and, thus, be formulated accordingly.

In certain embodiments, the thromboxane $A_2$ receptor antagonists may be formulated in a pharmaceutically acceptable oral dosage form. Oral dosage forms may include, but are not limited to, oral solid dosage forms and oral liquid dosage forms.

Oral solid dosage forms may include, but are not limited to, tablets, capsules, caplets, powders, pellets, multiparticulates, beads, spheres and any combinations thereof. These oral solid dosage forms may be formulated as immediate release, controlled release, sustained (extended) release or modified release formulations.

The oral solid dosage forms of the present invention may also contain pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof.

Depending on the desired release profile, the oral solid dosage forms of the present invention may contain a suitable amount of controlled-release agents, extended-release agents, modified-release agents.

Oral liquid dosage forms include, but are not limited to, solutions, emulsions, suspensions, and syrups. These oral liquid dosage forms may be formulated with any pharmaceutically acceptable excipient known to those of skill in the art for the preparation of liquid dosage forms. For example, water, glycerin, simple syrup, alcohol and combinations thereof.

In certain embodiments of the present invention, the thromboxane $A_2$ receptor antagonists may be formulated into a dosage form suitable for parenteral use. For example, the dosage form may be a lyophilized powder, a solution, suspension (e.g., depot suspension).

In other embodiments, the thromboxane $A_2$ receptor antagonists may be formulated into a topical dosage form such as, but not limited to, a patch, a gel, a paste, a cream, an emulsion, liniment, balm, lotion, and ointment.

DETAILED DESCRIPTION OF THE PREFERRED EMBODIMENTS

The following examples are not meant to be limiting and represent certain embodiments of the present invention.

Example 1

In this example, ifetroban sodium capsules are prepared with the following ingredients listed in Table 1:

TABLE 1

| Ingredients | Percent by weight |
| --- | --- |
| Na salt of Ifetroban | 35 |
| Mannitol | 50 |
| Microcrystalline Cellulose | 8 |
| Crospovidone | 3.0 |
| Magnesium Oxide | 2.0 |
| Magnesium Stearate | 1.5 |
| Colloidal Silica | 0.3 |

The sodium salt of ifetroban, magnesium oxide, mannitol, microcrystalline cellulose, and crospovidone is mixed together for about 2 to about 10 minutes employing a suitable mixer. The resulting mixture is passed through a #12 to #40 mesh size screen. Thereafter, magnesium stearate and colloidal silica are added and mixing is continued for about 1 to about 3 minutes.

The resulting homogeneous mixture is then filled into capsules each containing 50 mg, ifetroban sodium salt.

Example II

In this example, 1000 tablets each containing 400 mg of Ifetroban sodium are produced from the following ingredients listed in Table 2:

TABLE 2

| Ingredients | Amount |
| --- | --- |
| Na salt of Ifetroban | 400 gm |
| Corn Starch | 50 g |
| Gelatin | 7.5 g |
| Microcrystalline Cellulose (Avicel) | 25 g |
| Magnesium Stearate | 2.5 g |

Example III

In this example. An injectable solution of ifetroban sodium is prepared for intravenous use with the following ingredients listed in Tables 3a and 3b:

TABLE 3a

| Ingredients | Amount |
| --- | --- |
| Ifetroban Sodium | 2500 mg |
| Methyl Paraben | 5 mg |
| Propyl Paraben | 1 mg |
| Sodium Chloride | 25,000 mg |
| Water for injection q.s. | 5 liter |

TABLE 3b

| Ingredients | Amount |
| --- | --- |
| Ifetroban Sodium | 52.5 mg |
| Sodium Phosphate Dibasic Anhydrous | 345 mg |
| Sodium Phosphate Monobasic Anhydrous | 1.0 g |
| Sodium Chloride | 21.5 g |
| Water for injection q.s. | 5 liter |

The sodium salt of ifetroban, buffers and sodium chloride are dissolved in 3 liters of water for injection and then the volume is brought up to 5 liters. The solution is filtered through a sterile filter and aseptically filled into pre-sterilized vials which are then closed with pre-sterilized rubber closures. Each vial contains a concentration of 50 mg of active ingredient per 5 ml of solution.

Example IV

Right Ventricular Adaptation to Load Stress Improved by Thromboxane Receptor Antagonism Failure of the right ventricle to adapt to load stress is the direct cause of mortality in pulmonary arterial hypertension. Prostaglandin/thromboxane balance has been associated with cardioprotective effects under stress, probably through support of the coronary arteries.

Methods:

FVB/N mice or mice with a GFP macrophage-specific lineage tracing marker (LysM-Cre) underwent pulmonary banding to directly increase load stress (or sham surgery for controls), and starting the following day received either vehicle or the thromboxane receptor antagonist Ifetroban sodium in their drinking water (25 mg/kg/day). After 2 weeks, noninvasive hemodynamics were obtained by transthoracic echocardiography and invasive hemodynamics were obtained by pressure-volume catheterization of the right heart prior to sacrifice. Hearts were assessed for fibrosis and macrophage infiltration. RNA from right ventricles were isolated and used for unbiased discovery of altered gene expression using Affymetrix Mouse Gene 2.0 arrays performed on four groups (banded or sham). LysM-Cre mouse hearts were flash-frozen whole, cross-sectioned, and assessed by microscopy for fibrosis and macrophage infiltration. Differences between groups were assessed by ANOVA and t-tests. Correlations were assessed by Spearman correlation.

Results:

Banded mice receiving ifetroban showed hemodynamic markers of preserved right heart function under load stress, associated with a reduction in fibrosis and reduction in recruitment of inflammatory cells. The molecular basis for these effects, based on expression arrays, rested on reduction of pro-fibrotic pathways such as PDGF-D and FBXO32, and induction of anti-fibrotic pathways including THBS4 and TGF-beta inhibitors Asporin and LTBP2. There was also evidence of induction of pathways related to functional hypertrophy, including potential increases in angiogenesis and reactivation of a developmental program associated with cardiac myogenesis. All of these changes were specific to banded mice, and were not found in the sham surgery group that received Ifetroban sodium. Since load stress has previously been shown to induce thromboxane production, this is likely because the pathways blocked by the drug were not active in sham surgery.

Conclusions:

Rodent models of right ventricular load stress to demonstrate that physiologic and molecular markers of adaptive response are improved by the thromboxane receptor antagonist ifetroban sodium.

Example V

The purpose of this study was to determine whether ifetroban-mediated blockade of the thromboxane-prostanoid receptor can affect cardiac/pulmonary function and gene expression in a mouse model of pulmonary hypertension, in order to determine whether ifetroban is useful to treat pulmonary hypertension in humans with early stages of the disease.

Experimental Methods: In this pulmonary artery banding (PAB) animal model, we used wildtype or Rosa26-rtTA2 mice on a normal diet. Mice were anesthetized and subject to either PAB (20 mice) or sham surgery (10 mice) at 4-6 months of age. Following the procedure, the mice were given either ifetroban water at 30 mg/kg/day or normal drinking water, and after 14 days of treatment we performed cardiovascular phenotyping followed by terminal sacrifice, histology and gene expression arrays.

Echocardiograms to assess cardiac output were obtained the day prior to catheterization and sacrifice. Our standard cardiovascular phenotyping continued with systemic pressure measurement by tail vein cuff, and intrajugular heart catheterization with measurement of right ventricular systolic pressure (RVSP) for peak pressure, diastolic pressure, diastolic time constant, arterial elastance, ejection fraction, and stroke volume.

Following sacrifice, right ventricular hypertrophy was assessed in each animal as a percentage of heart weight. A random fraction of the right hearts were fixed in formalin for histology and examined for indices of fibrosis; other hearts were snap frozen for gene expression analysis via RNA microarray. Right hearts and lungs were collected for analysis of protein expression and gene expression array. Left lungs were fixed and stained. Platelet deposition was examined in small pulmonary artery vessels. The remaining organs were harvested and frozen in liquid nitrogen for potential gene expression analysis.

The results obtained were as follows. The banding of the pulmonary artery was successful (i.e., right ventricular systolic pressure (RVSP) increased), but ifetroban did not have an effect. Total cardiac output was essentially unchanged following banding, indicating right heart compensation. The ratio of Tricuspid E to A Wave ($p<0.05$ by unpaired t test) demonstrated that ifetroban significantly increased the ratio of the tricuspid E to A wave in banded mice. This data suggests that ifetroban increases the size of the heart in the midst of a fibrotic stressor, which could be beneficial. The results also demonstrate that treatment with Ifetroban decreases fibrosis in banded right ventricles. A cross-section of the right ventricle in the mice (trichrome-stained RV taken at 20×) showed that ifetroban reduced fibrosis in the right ventricle for both the sham surgery and the banded right ventricle. Vehicle treated mice had increased levels of fibrotic collagen deposits while ifetroban-treated mice showed very little fibrosis.

Genes altered by pulmonary banding and Ifetroban treatment fit into three general categories: inflammation, fibrosis, and muscularization. In general, all three are increased by banding, but treatment with Ifetroban decreases expression of pro-fibrotic and inflammatory genes, and increases expression of pro-muscularization genes.

As part of this study, RNA extracted and expression analysis was performed using Mouse Genone 2.0 Affymetrix expression arrays. (FIG. 4C). The Array design was 2×2×2: Sham/Banded×Vehicle/Ifetroban×M/F. In total, there were 8 arrays; each array was a pool of RV from 3 mice. Only mice with an RVSP>30 were used for the banded groups. Banding itself altered 199 genes (ABS (Diff in averages)—Sum of standard deviations)>0.4 comparing vehicle banded to sham, and expression of 49 of those genes was enhanced by ifetroban (difference >0.4) and expression of 29 of those genes was attenuated by ifetroban (difference >0.4). Of the genes whose increase is blocked by ifetroban, it is assumed that about half indicate reduced inflammatory cell recruitment, based on the fact that (i) ifetroban reduces the expression of PDGF, a profibrotic signaling molecule (Ponten, et al., Platelet-derived growth factor D induces cardiac fibrosis and proliferation of vascular smooth muscle cells in heart-specific transgenic mice" Circ. Res. 2005 Nov. 11:97 (10): 1036-45); (ii) with respect to fibrosis/anti-fibrosis, ifetroban reduces the expression of FBX032, a profibrotic signaling molecule (Usui, et al., "Endogenous muscle atrophy F-box mediates pressure overload-induced cardiac hypertrophy through regulation of nuclear factor-kappaB", Circ. Res., 2011 Jul. 8 09(2): 161-71); (iii) with respect to fibrosis/anti-fibrosis, ifetroban enhances the expression of certain genes related to collagen and cell-cell adhesion, particularly thrombospondin-4 (Thbs4). Of genes whose increase was enhanced by ifetroban, about half are related to collagen and cell-cell adhesion; (iv) ifetroban also enhanced the expression of genes involved with the inhibition of TGF-Beta, Asporin and Ltbp2; (v) ifetroban enhances the expression of other genes, i.e., Nmrk2, Meox1, Nkd2, and Pkhd1; (vi) with respect to muscularization, ifetroban enhances the expression of NMRK2, which may play a key role in controlling the progression of muscle differentiation (Li, et al. "A novel muscle-specific beta 1 integrin binding protein (MIBP) that modulates myogenic differentiation), J. Cell Biol. 1999 Dec. 27: 147(7); 1391-8; (vii) with respect to muscularization, ifetroban enhances expression of Meox1 (Mankoo, et al., "The concerted action of Meox homeobox genes is required upstream of genetic pathways essential for the formation, patterning and differentiation of somites", Development, 2003 October: 130(19):4655-64; ifetroban enhances the expression of NKD2, Hu, et al., "Myristoylated Naked2 antagonizes Wnt-beta-catenin activity by degrading Dishevlled-1 at the plasma membrane", J. Bio. Chem. 2010 Apr. 30: 285(18) pp 0.13561-8, see FIG. 12; ifetroban enhances the expression of Pkhd1 (Gilles sen-Kaesbach, et al., "New autosomal recessive lethal disorder with polycystic kidney type Potter I, characteristic face, microephaly, brachymelia, and congenital heart defects", AM J Med Genet., 1993 Feb. 15; 45(4):511-8.

Therefore, the protective effects of ifetroban in RV stress may include reduction in recruitment of inflammatory cells; reduced induction of pro-fibrotic pathways such as PDGF-D and FBXO32; induction of anti-fibrotic pathways including THBS4 and TGF-beta inhibitors Asporin and LTBP2; and induction of pathways related to functional hypertrophy, including potentially angiogenesis.

Example VI

Wild-type mice underwent pulmonary artery banding followed by two weeks or six weeks of treatment with ifetroban (30 mg/kg/day via the drinking water) vs. control (plain drinking water). The pulmonary artery band mimics pulmonary hypertension and right heart failure. Right heart histology revealed significantly increased cardiomyocyte size in the control mice, and ifetroban treatment was able to prevent this effect and showed similar cardiomyocyte size to animals that underwent sham surgery.

Echocardiography after 6 weeks of treatment/pulmonary artery banding revealed left ventricular failure in the control mice while ifetroban treated mice had cardiac function values similar to the animals that underwent sham surgery.

Right ventricular systolic pressure (RVSP) was first shown to be elevated in all of the animals which had received the pulmonary artery band (as expected). Echo data (including end diastolic volume, end systolic volume, left ventricular stroke volume, ejection fraction and fractional shortening) at 6 weeks revealed that the left ventricle was failing in the vehicle-treated PAB mice, while the ifetroban-treated PAB mice were protected from these effects and had echo values similar to sham surgery animals. The fact that by extending pulmonary artery banding out to 6 weeks there was left ventricular failure that wasn't seen in the 2 week model is considered to be surprising, and makes ifetroban's ability to protect against this left ventricular failure even more striking. Ifetroban also protected against increases in cardiomyocyte diameter in the right ventricle and reduced right ventricular fibrosis at 6 weeks.

These results suggest that ifetroban provides protection from dilated cardiomyopathy in this 6 week model via multiple mechanisms/pathways.

Example VII

Given the predominantly deleterious consequences of TP receptor activation in conditions of cardiac stress, and the production of isoprostanes associated with cardiomyopathy, we examined the effects of TP receptor antagonism in a pulmonary artery banding (PAB) model of right ventricular pressure overload. In this Example, mice with RV dysfunction due to pressure overload by pulmonary artery banding (PAB) were given vehicle or ifetroban. Two weeks following PAB, ifetroban-treated mice were protected against pressure overload. Gene expression arrays, quantitative histology and morphometry, lineage tracing, and cell culture systems were used to determine the mechanism of ifetroban protection. Ifetroban caused a near normalization of fibrotic area, prevented cellular hypertrophy while allowing increased RV mass, increased expression of anti-fibrotic thrombospondin-4, and blocked induction of the pro-fibrotic TGF-beta pathway. Low-dose aspirin failed to replicate these results. Extending treatment with TP receptor antagonist to 6 weeks after PAB led to more functional adaptation and decreased indications of cardiac failure seen with prolonged pressure overload.

Both male and female age-matched C57Bl/6 or FVB/NJ mice, obtained by in-house breeding, were used for pulmonary artery banding. LysM-GFP mice were obtained by cross-breeding LysM-Cre×mTomato/GFP reporter mice B6.129P2-Lyz2tm1(cre)Ifo/J (a gift from Tim Blackwell)× Gt(ROSA)26Sortm4(ACTB-tdTomato, -EGFP)Luo (JAX stock #007676). The day following surgery, mice were given either 25 mg/kg/day IFETROBAN (Cumberland Pharmaceuticals Inc., Nashville, TN) in drinking water or normal drinking water (vehicle) for 2 weeks or 6 weeks prior to hemodynamic evaluation. Mice were weighed and water was changed once a week.

Results: Increased Ventricular Efficiency in PAB Mice Receiving Ifetroban

Mice underwent pulmonary arterial banding (PAB) or sham surgery, and were treated for 2 weeks with vehicle or ifetroban (competitive antagonist of TPα/TPβ) in the drinking water. Right ventricular systolic pressure (RVSP) was elevated in PAB mice, indicating successful mechanical vasoconstriction. At two weeks post-banding, there was no significant change in cardiac output, and RV mass similarly increased in vehicle- and ifetroban-treated PAB groups. However, by echocardiography, the E/A wave ratio was increased in mice given TP antagonist, suggesting increased filling efficiency. TP receptor expression in the RV was analyzed by Western blot, and remained constant after 2 weeks following PAB or drug treatment.

PAB induced an increase in RVSP from ~22 mm Hg to approximately 40 mm Hg (, $p<0.01$ by two-way ANOVA). Cardiac output was not reduced in PAB mice after 2 weeks. The ratio of right ventricular weight to left ventricle+septum weight increases in PAB mice (, $p<0.01$ by two-way ANOVA); this increase is not blocked by ifetroban. Tricuspid E/A wave ratio, a measure of contractility, is improved by ifetroban (*, $p<0.05$ by ANOVA), but only in PAB mice. TP receptor protein is expressed in whole RV, and expression does not change with PAB.

Decreased Cardiac Fibrosis with TP Receptor Antagonism

An RVSP of 30 mmHg was used to define PAH, and only samples from mice at or above this threshold were used for analysis of PAB groups. PAB mice developed significant RV fibrosis by 2 weeks, which was almost completely abolished with ifetroban treatment. An oral dose of aspirin (10 mg/kg/day), failed to prevent fibrosis in this model suggesting that thromboxane A2 is not the ligand mediating fibrosis. Two weeks after PAB, fibrosis in the RV of untreated mice has increased from <5% to ~20% (blue stain) in histologic sections of frozen RV stained with Masson's trichrome. This effect is blocked by ifetroban, but not by aspirin.

Changes in RV Gene Expression in Ifetroban-Treated PAB Mice

To determine the mechanism through which ifetroban reduced fibrosis and protected RV contractility, we performed gene expression arrays on sets of pooled RV from mice with sham or PAB surgery, with and without drug treatment. By principal components analysis strong effect of banding was found, and an effect of ifetroban only in mice that had undergone banding. Principal Components Analysis shows strong separation of groups with banding, with a strong effect of ifetroban only in mice with banding. Ifetroban did not significantly change gene expression in mice with only sham surgeries. In PAB mice, ifetroban treatment enhanced transcription of some genes, while the effect of banding on other genes was blocked with TP receptor antagonism. In particular, there were changes in gene expression associated with adhesion, collagen organization, extracellular structure, and developmental processes.

Cardiac Monocytes in PAB Mice

By expression array, PAB mice given ifetroban had decreased RV expression of Cd14, a marker for mature macrophages, as well as Tlr8 and other pro-inflammatory genes. TP receptors are also expressed on monocytes, and blockade of these receptors may have immune-specific effects. To determine whether the decrease in fibrosis seen with TP receptor inhibition was due to decreased macrophage infiltration or proliferation in the RV, PAB on LysM-Cre mice expressing eGFP under the LysozymeM promoter was performed, where all cells that have ever had monocyte lineage are labeled with GFP, even if they have later differentiated. While the majority of monocytes were located in the left heart or septum, PAB appeared to increase the number of RV monocytes in vehicle-treated and aspirin-treated mice. Flow cytometry of RV taken from wildtype mice revealed no significant changes with banding in any macrophage population examined, with a non-significant trend toward increased CD14/CD45 and F480/CD45-labeled cells and decreased CD86-labeled CD45+ cells in vehicle-treated, but not ifetroban-treated PAB mice compared to sham-operated controls. This mismatch to the LysM-Cre mice suggests that the cells lose their circulating differentiation markers upon lodging in the heart. Gene expression arrays showed ifetroban reduced expression of genes associated with inflammatory cell recruitment, but only in the context of pressure overload. Transgenic LysM-Cre×flox-mTomato-flox eGFP mice were used to label cells of monocyte derivation in the RV. These mice express a fluorescent red, except in cells derived from monocyte lineage (even if they have later differentiated), which express a fluorescent green. PAB significantly increases numbers of green cells in vehicle and ASA mice, but not in ifetroban-treated mice (representative images from 2-3 transgenic hearts shown). Flow sorting of whole RV for circulating markers found a non-significant trend towards an increase in PA-banded mice that was blocked by ifetroban.

Decreased Cellular Hypertrophy in IFETROBAN-Treated PAB Mice

Expression of genes associated with myogenic differentiation was enhanced in PAB mice receiving TP receptor antagonist compared to banded controls. Although RV weight increased similarly in vehicle-treated and ifetroban-treated PAB mice, the increase in cardiomyocyte diameter normally associated with PAB was blocked with ifetroban treatment. Aspirin-treated mice had cardiomyocyte diameters similar to vehicle-treated mice. Cardiomyocyte size increases in mice with PAB. This effect is blocked by ifetroban, but not by aspirin. Western blot demonstrated α-MHC and β-MHC expression in RV. α-MHC is variable, but unchanged, while β-MHC is strongly induced in PAB mice given the TP receptor antagonist. Ifetroban treatment of PAB mice caused an induction of ß-myosin heavy chain (ß-MHC) protein with no change in α-MHC expression. In an aortic banding model of pressure overload, this induction is associated with decreased individual hypertrophy in ß-MHC-expressing cells. The induction of ß-MHC after TP receptor antagonism was not due to increased animal age, as the average ages of vehicle-treated and ifetroban-treated PAB mice were 688.3±19.8 and 689.8±18.5 days, respectively. Gene expression arrays showed ifetroban-induced genes associated with adaptive remodeling, but only in the context of pressure overload.

Decreased TGF-ß Signaling and Enhanced TSP-4

The effect of ifetroban treatment on known fibrotic and anti-fibrotic signaling pathways was examined. Mice receiving the TP receptor antagonist had less phospho-SMAD2/3 associated with PAB than vehicle-treated mice, and reduced expression of genes associated with fibrosis, with increased expression of antifibrotic genes. Ifetroban-treated cultured cardiomyocytes given exogenous TGF-ß had no change in PAI-1 expression or promoter activity compared to vehicle-treated cells, indicating no direct blockade of TGF-ß signaling from its receptor and suggesting that the in vivo block of TGF-β occurs upstream of ligand binding. Opposing the pro-fibrotic TGF-ß, pressure overload is associated with an induction of antifibrotic thrombospondin-4 (Thbs4; TSP-4) mRNA. Ifetroban treatment strongly enhances Thbs4 expression in PAB RV only (FIG. 6B), which translates to increased TSP-4 protein in ifetroban-treated banded mice. While localization of TSP-4 appeared to be confined to fibrotic patches in vehicle-treated RV, PAB mice receiving ifetroban demonstrated increased cardiomyocyte expression of TSP-4. Ifetroban blocks phosphorylation of TGF-β signaling molecule Smad2/3 in vivo (each band is from a different mouse heart). Gene expression arrays from RV showed ifetroban reduced profibrotic genes and induced antifibrotic genes, but only in the context of pressure overload. In cultured cardiomyocytes, ifetroban does not block protein expression of canonical TGF-β target PAIL, nor does it block induction of a luciferase activity driven by a PAH promoter. PAB induces TSP-4 expression in RV, which is strongly enhanced with ifetroban treatment.

Prevention of Cardiac Failure

In the previous experiments, there was an increase in RV mass but not yet any change in cardiac output or other functional parameters, apart from E/A wave ratio, following PAB. To determine whether the decrease in fibrosis seen with TP receptor antagonism leads to increased preservation of cardiac function, the period following PAB-induced pressure overload was extended to 6 weeks and dosing with ifetroban was continued to 6 weeks, as well. After 6 weeks, control-treated PAB mice developed left ventricular dilation, as demonstrated by increased systolic and diastolic volume, which was accompanied by a compensatory increased stroke volume. This was associated with a decreased ejection fraction and decreased fractional shortening, signs of cardiac failure. All of these were prevented in PAB mice that received ifetroban, despite similar RVSP. Mice underwent sham surgery or PAB and echocardiography and pressure-loop catheterization performed after 6 weeks. End diastolic and systolic volume of the left ventricle were measured using the average of values calculated using both spherical and cylindrical models. Also obtained from echocardiography were the left ventricular stroke volume and ejection fraction, as well as percent fractional shortening.

Comparison of High Dose Versus Low Dose Ifetroban

In another arm of this example, low dose (3 mg/kg/day) ifetroban was administered to mice via the drinking water for 2 weeks following pulmonary artery banding. Right ventricular histology revealed that this low dose treatment does not prevent fibrosis of the right ventricle. In addition to fibrotic collagen deposition, nuclei were present in the extracellular space from infiltrated or proliferating cells. The previously presented results herein revealed an antifibrotic effect of high dose ifetrobn (25 mg/kg/day) in the same model. Densitometry analysis of thrombospondin-4 (TSP-4) Western Blots of right ventricular tissue demonstrate that high dose ifetroban (25 mg/kg/day) given via the drinking water for 2 weeks following pulmonary artery banding increases the expression of antifibrotic TSP-4 while low dose ifetroban 3 mg/kg/day does not.

Discussion

The effect of TP receptor antagonism was studied in mice with mechanical constriction of the pulmonary artery, a model of PAH-associated RV hypertrophy. Treatment with the an effective amount of the TP receptor antagonist ifetroban reduced RV fibrosis and cardiomyocyte hypertrophy in PAB mice, and increased E/A ratio, one indicator of cardiac efficiency (The E/A ratio is the ratio of the early (E) to late (A) ventricular filling velocities. In a healthy heart, the E velocity is greater than the A velocity. In certain pathologies and with aging, the left ventricular wall can become stiff, increasing the back pressure as it fills, which slows the early (E) filling velocity, thus lowering the E/A ratio). This was associated with augmented RV expression of anti-fibrotic and muscularization genes, as well as decreased expression of genes associated with inflammation and a decrease in RV phospho-SMAD2/3. Few differences were found in sham-operated mice receiving ifetroban, indicating that ifetroban-mediated gene expression changes are specific to PA banding. When the pressure overload was extended to 6 weeks, mice given TP receptor antagonist were protected from the indications of cardiac failure seen in vehicle-treated PAB mice: gross increases in left ventricular volume as well as decreases in ejection fraction and fractional shortening. This may be due to ventricular interdependence, septal bowing, or neurohormonal activation.

The initial cardioprotective effects seen with TP receptor antagonism were not duplicated with low-dose aspirin treatment of mice; suggesting that the fibrosis associated with PAB is not mediated by platelet-generated thromboxane. This low dose was chosen because high-dose aspirin in patients with heart failure does not decrease mortality or hospitalization, and to avoid confounding anti-inflammatory or salicylate-mediated NF-κB effects. There does remain the possibility that either local or macrophage production of $TxA_2$ is responsible for the cardiac fibrosis observed in this model. However, isoprostanes such as 8-iso-$PGF_{2\alpha}$, are also known to signal through the TP receptor, and can cause increased collagen production and fibrogenic effects. Indeed, reducing oxidative stress and isoprostane generation through enhancement of superoxide dismutase or introduction of free radical scavengers can have antifibrotic, cardioprotective effects in pressure-overload. There is some debate over which specific isoprostanes signal through the TP receptor or whether a structurally similar "TP-like receptor" mediates some isoprostane action. It is possible that tissue-specific receptor complexes may form, or there is a yet-unidentified TP-like receptor with similar binding that may play a role in the effects of Ifetroban. Alternatively, besides isoprostanes and thromboxane, the effects of ifetroban could be mediated by another endogenous ligand for the TP receptor, such as prostaglandin $H_2$ or 20-HETE.

To further complicate matters, there are α and ß isoforms of the TP receptor, splice variants with similar ligand binding and $G_q/G_{11}$ coupling but differing localizations. Both receptors are effectively blocked by ifetroban. It is currently unknown which of these isoforms, and on which tissue, mediates cardiac fibrosis in response to pressure-overload. By both immunoblotting and mRNA (data not shown), we detected robust TP receptor expression in whole RV, which suggests its expression in cardiomyocytes, although the possible contribution of fibroblast or endothelial receptors cannot be ignored. However, our methods were unable to distinguish between TPα and TPβ expression.

In this study, we also examined the effects of TP receptor inhibition on RV macrophage number and cell marker expression in PAB mice. By FACS analysis we did not find any significant changes, not only with ifetroban treatment compared to vehicle, but also between PAB and sham-operated mice. However, in hearts taken from mice with GFP-expressing cells of monocyte lineage, there appeared to be many monocytes that were well-integrated with cardiomyocyte fibers, and it is possible that we did not completely dissociate individual monocytes from each RV. It is also possible that the LysM-expressing cells visualized in the transgenic hearts were actually neutrophils, although by FACS the percentage of total CD45-expressing cells, which would include neutrophils, did not change.

At 2 weeks post-PAB, ifetroban treatment increased the E/A wave ratio in PAB mice, indicating possible increased contractile efficiency. This is similar to a previous study, demonstrating that TP receptor antagonism preserves RV efficiency following endotoxic shock (Lambermont B, Kolh P, Ghuysen A, Segers P, Dogne J M, Tchana-Sato V, Morimont P, Benoit P, Gerard P, Masereel B and D'Orio V. Effect of a novel thromboxane A2 inhibitor on right ventricular-arterial coupling in endotoxic shock. *Shock.* 2004; 21:45-51). It is unknown whether this increased efficiency with ifetroban treatment is due to the decrease in cardiac fibrosis, or the decrease in cardiomyocyte hypertrophy associated with PA banding, or perhaps a combination of these two mechanisms. The decreased cellular hypertrophy we find with ifetroban is consistent with the known hypertrophic effects of TP receptor activation in mice, but is likely a concerted in vivo effect and not due to direct TP receptor inhibition on cardiomyocytes, as a thromboxane agonist did not cause hypertrophy of isolated cardiomyocytes in vivo.

The prevention of individual cellular hypertrophy and concomitant increased RV expression of ß-MHC in TP antagonist-treated PAB mice, with no change in α-MHC expression, corresponds with a previous study by Lopez et al (Lopez J E, Myagmar B, Swigart P M, Montgomery M D, Haynam S, Bigos M, Rodrigo MC and Simpson PC. ß-Myosin heavy chain is induced by pressure overload in a minor subpopulation of smaller mouse cardiac myocytes. *Circ Res.* 2011; 109:629-38). By size-sorting individual cardiomyocytes following pressure overload, they found that ß-MHC expression only occurred in non-hypertrophic cardiomyocytes; all cells had similar α-MHC expression. Although individual cells did not increase in diameter, PAB mice given ifetroban had similar increases in RV weight as vehicle-treated mice, as evidenced by increased Fulton index. Among the genes activated by Ifetroban in conjunction with banding were a number of genes associated with cell growth and reprogramming, and it is theorized that TP receptor inhibition induces muscularization and functional hypertrophy in response to pressure overload, while also decreasing the fibrotic response. Decreased TGFß activity is probably partially responsible for the decreased fibrotic response, although the ifetroban-initiated event behind the decrease in TGFß is yet unknown.

TSP-4, which is increased by PA banding and further upregulated with ifetroban treatment, is not known to regulate TGFß activation but itself can decrease fibrosis and hypertrophy, and increase contractility and cardiac adaptation in pressure overload. TSP-4 is thought to act by inducing protective endoplasmic reticulum (ER) stress signaling via activating transcription factor 6α (Atf6α), an ER stress response transcription factor. While the localization of TSP-4 to cardiomyocytes in ifetroban-treated mice, as opposed to strictly fibrotic areas in vehicle-treated mice, would support intracellular signaling, in our model, there was no difference in Atf6α mRNA levels either after PA banding or TP receptor antagonism (data not shown). It is entirely possible that the 2-week timepoint missed any increase in mRNA, or that the RV stress response differs from the LV model where the Atf6α response to TSP-4 was delineated.

In summary, these studies demonstrate that ifetroban is cardioprotective against pressure overload, by moving the right heart towards adaptation rather than a maladaptive fibrosis, inflammation and cellular hypertrophy. Protection of the right heart eventually leads to prevention of left heart failure in these mice.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification is to be regarded in an illustrative manner rather than a restrictive sense.

What is claimed is:

1. A method of treating pulmonary arterial hypertension in a human in need of treatment thereof, comprising administering a therapeutically effective amount of [1S-(1α,2α,3α,4a)]-2-[[3-[4-[(Pentylamino)carbonyl]-2-oxazolyl]-7-oxabicyclo[2.2.1]hept-2-yl]methyl]-benzenepropanoic acid (ifetroban) or a pharmaceutically acceptable salt thereof to the human.

2. The method of claim 1, wherein the pulmonary arterial hypertension is associated with systemic sclerosis.

3. The method of claim 1 wherein the therapeutically effective amount is from 10 mg to 1000 mg per day.

4. The method of claim 3, wherein the ifetroban or the pharmaceutically acceptable salt thereof is administered orally, intranasally, rectally, vaginally, sublingually, buccally, parenterally, or transdermally.

5. The method of claim 4, wherein the ifetroban or the pharmaceutically acceptable salt thereof is administered orally.

6. The method of claim 3, wherein the therapeutically effective amount is 250 mg per day.

7. The method of claim 1, wherein the pharmaceutically acceptable salt of ifetroban is ifetroban sodium.

8. The method of claim 7, wherein the ifetroban sodium is in an oral solid dosage form.

9. The method of claim 8, wherein the therapeutically effective amount is 250 mg per day.

10. The method of claim 3, wherein the therapeutically effective amount is from 100 mg to 500 mg per day.

* * * * *